United States Patent [19]

Seppo

[11] 4,054,955

[45] Oct. 25, 1977

[54] ORTHOPAEDIC ENDOAPPARATUS DESIGNED TO GROW A NEW LIVE SHOULDER AND HIP JOINT, TO RECONSTRUCT A DEFORMED JOINT OR TO RESTORE A PATHOLOGICALLY DYSPLASTIC AND CONGENITALLY LUXATED JOINT

[76] Inventor: Arnold Ivanovich Seppo, ulitsa Taara 4, Tallin, U.S.S.R.

[21] Appl. No.: 653,544

[22] Filed: Jan. 29, 1976

[51] Int. Cl.$^2$ .................... A61F 1/24; A61F 5/00
[52] U.S. Cl. .................... 3/1.91; 3/1.912;
128/69; 128/92 C; 128/92 CA
[58] Field of Search .................... 3/1, 1.9–1.913;
128/92 C, 92 CA, 92 BC, 92 R, 92 G, 69, 78

[56] References Cited

U.S. PATENT DOCUMENTS

| | | | |
|---|---|---|---|
| 2,765,787 | 10/1956 | Pellet | 128/92 CA |
| 3,242,922 | 3/1966 | Thomas | 128/92 R |
| 3,680,553 | 8/1972 | Seppo | 128/92 BC |

OTHER PUBLICATIONS

"Correction of Subluxation of the Tibial Head", The Journal of Bone & Joint Surgery, vol. 18, No. 2, Apr. 1936, p. 511.

*Primary Examiner*—Ronald L. Frinks
*Attorney, Agent, or Firm*—Steinberg & Blake

[57] ABSTRACT

The orthopaedic endoapparatus designed to grow a new live shoulder and hip joint, to reconstruct a deformed joint or to restore a pathologically dysplastic and congenitally luxated joint, contains a figured hinge, consisting of a spherical knob engaged with a curved guiding member. The spherical knob is linked by an expandable connecting turnbuckle with an anchor-like pair of curved rods to secure the fixation of the endoapparatus to the hip or shoulder bone, while the guiding member is connected with an anchor-like member fastening the endoapparatus to the pelvis or to the scapula and clavicula. The endoapparatus allows one to connect the joint ends of the bones purposefully with regard to kinematics, maintaining during rest as well as during movements, effected in the provisional joint around a predeterminate point or some axes, a clearance between the faciae articularis indispensable for their conjunctive, congruent and complementary growth, terminated in covering the faciae articularis with a layer of supporting hyaline cartilage of the joint.

6 Claims, 6 Drawing Figures

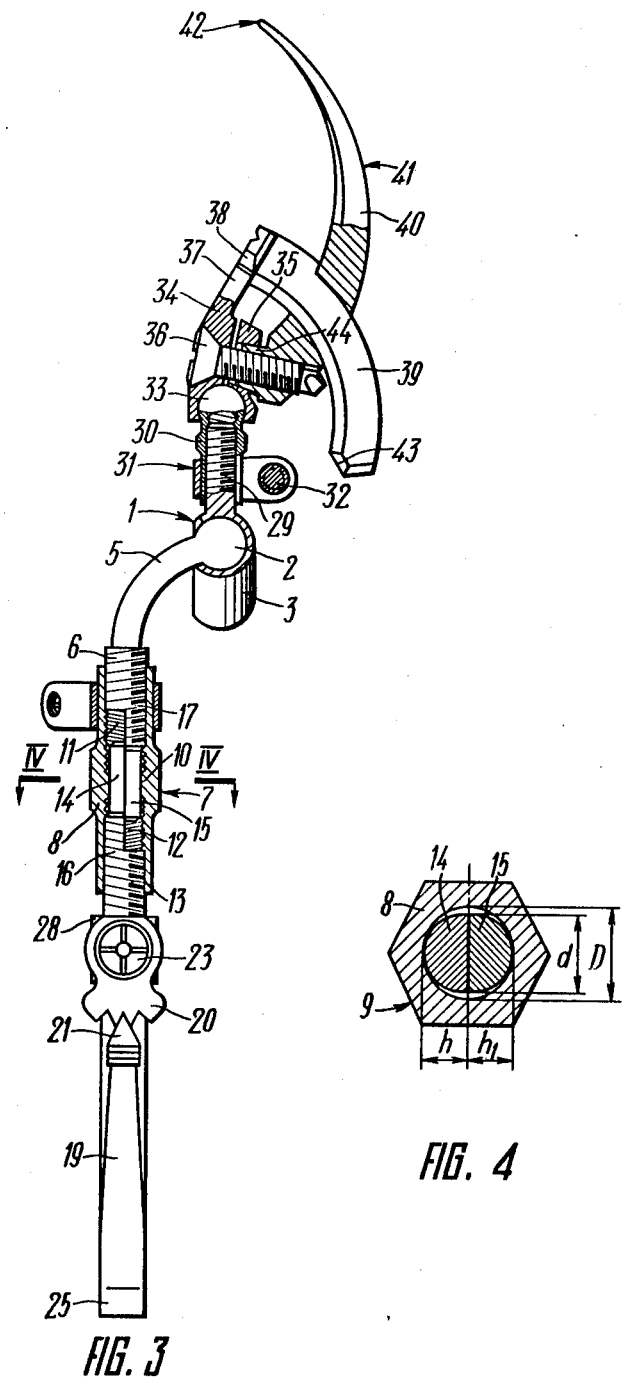

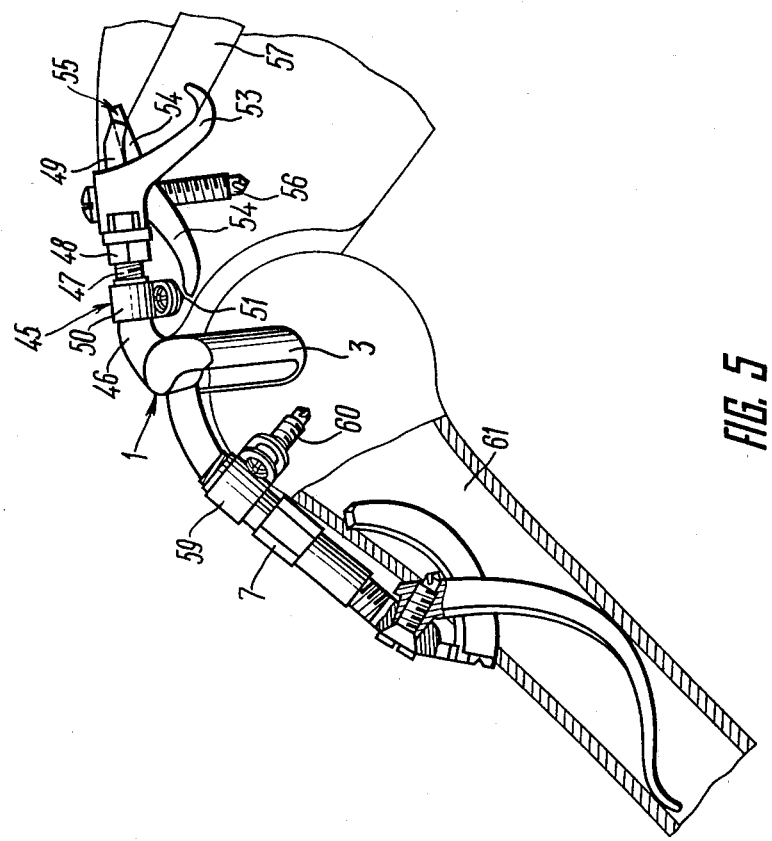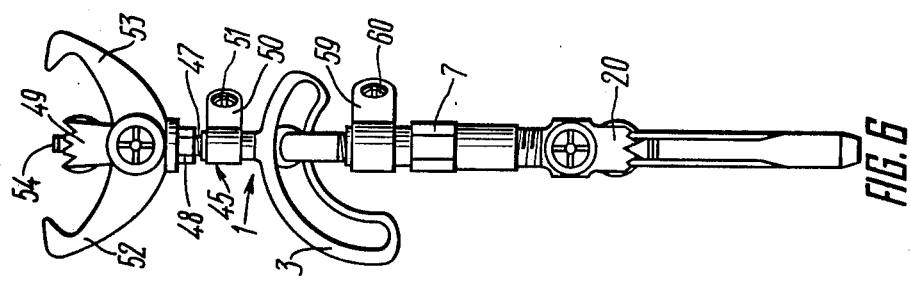

ORTHOPAEDIC ENDOAPPARATUS DESIGNED TO GROW A NEW LIVE SHOULDER AND HIP JOINT, TO RECONSTRUCT A DEFORMED JOINT OR TO RESTORE A PATHOLOGICALLY DYSPLASTIC AND CONGENITALLY LUXATED JOINT

The present invention relates to surgical apparatus used in orthopaedics and traumatology, and more particularly to an orthopaedic endoapparatus designed to grow a new live shoulder or hip joint, to reconstruct a deformed joint or to restore a pathologically dysplastic and congenitally luxated joint.

By its structure and function the skeleton system is the locomotor system of the human body. It consists of bones, acting as levers, and of their moving connections, the joints.

The locomotor system is made to move by muscular strength activated by human will. Muscles that set it into motion are attached to bones which form the joints, the basic muscles having their points of fixation near the ends of the joints. The volitional impulse to move is passed on to the muscles by way of the nervous system only if the nerve bundles of the muscles are intact, the intended movement may be strong, precise and agile only if the shape and structure of the surfaces of the joint correspond to the intended function. Damage to one or all enumerated components caused by a pathological process or a traumatic surgical operation impairs or ruins the functioning of the respective joint. The larger it is and the more important its specific function, the greater is the loss of working capacity sustained by man through the cessation of its functioning. The loss of the shoulder joint impairs the capacity to work, but a particularly grave loss is caused to man if his hip joint is ruined. In adolescence ankylosis of the hip joint may also lead to the deformation of the spine and asymmetry of the pelvis. Worse still, ankylosis of both hip joints shuts man out altogether from family life and work, and prevents him from complying with the elementary demands of personal hygiene. In other words, for a man in this pathological condition it becomes physically impossible to exist as an equivalent member of human society.

To alleviate the gravity of such personal tragedies surgeons at all stages of the development of orthopaedics and reconstructive surgery have been trying to help those patients.

With the introduction of immobilization as a method of healing injuries or diseases of the human skeleton, there appeared as a natural consequence ankylosis of the joints. Immobilization was later supplemented by the resection of the joint ends of the bones with the result of speeding up the appearance of ankylosis.

The grave damage caused to the functioning of the locomotor system after the ankylosis of a large joint impelled the orthopaedians to search for means allowing one to reconstitute at least some kind of motion as a substitute for the lost joint.

Inability to set growing new live articular hyaline cartilage pushed surgeons into a blind alley, the insertion of various laminae, supposedly able to replace hyaline cartilage. Scrutiny of post-operational effects showed, however, that tissue which has been placed between the joints, while occasionally taking on, as in the case of false joints, a grist-like appearance, did not have the typical structure of cartilage.

The absence of support-giving hyaline cartilage of the joint as the basic structural element of a live natural joint did not allow one to secure by means of such operations the desired effect of the functional restoration of the limb.

The failure in the use of laminae between the ends of the joint provoked surgeons even in our time to repeat the experiments made by E. Lexer in attempting to replace lost joints by homotransplants taken from corpses and, finally, by alloplastic endoprostheses.

Special research as well as clinical practice have demonstrated that dead material of whatever origin does not coalesce with live human tissue, be it muscles or bones. On the contrary, homotransplants become separated from live tissue by a thin bluish-white coating of connective tissue. After a while the necrotic bone deteriorates, poisoning the human organism by the products of its decay.

The alloplastic endoprosthesis is a metallic joint placed by the surgeon into the human organism instead of the pathologically transformed natural joint. This endoprosthesis is attached to bone fragments by means of supporting members.

The trochanteric part of the thigh-bone, into which the supporting member of the coxal endoprosthesis is introduced, has the appearance of a vortex of irregular shape flattened in the anteroposterior direction. The fragile compact coating of the bone, thinning out upwards to 1 mm, forms the outer stratum of the vortex wall, backed from inside by the spongy trabecular system, to which the relative solidity of this bone vortex is largely due. The central zone of the spongy bone of the trochanter, upon which the supporting member of the endoprosthesis, introduced without cement, is leaned, gets crushed, in the case of elderly patients, on the average under a pressure of $\delta = 13.2$ kg/cm$^2$. It follows that the supporting member of the endoprosthesis is meeting here almost no resistance against the rotational moment of dislodging forces. The contacting tension of variable magnitude, due to the bending moment of the forces originated from movements of the extremity, also exceeds the resistibility to pressure. As soon as the patient leans upon his leg, the system becomes destructive, as the tension exceeds the resistibility to pressure of the spongy substance of the bone. This leads to the gradual wearing down of the immobility of the contact between the bone and the endoprosthesis. The attempt to correct this by introducing cement between the supporting member of the endoprosthesis and the bone tissue resulted in the opposite extremity. In this operation the entire spongy structure of the vortex including blood vessels and nerves is being removed. This leaves the remaining layer of the bony vortex brittle and to a large extent devitalized. The bone therefore sometimes breaks soon after the operation. The same consequences take place in the cases of similar treatment of shoulder-bone.

The lengthiness and extensive traumatism of the prosthesis application procedure (36 successive stages) invariably produces unavoidable and fatal complications of a cardiovascular, regenerative and infective nature. The shakiness of the endoprosthesis, fracturings of the bone and wound infection dictate removal of the endoprosthesis. After this has been done, there remains an irreparable defect of the bone and the joint. The extremity is deprived of its support.

The insertion of protheses is altogether impossible in adolescence, when the restoration of the movability of the lost joint is even of greater importance than in advanced age.

It follows that the problem of restoring the mobility of joints remains imperfectly solved even by this costly and most hazardous method of prostheses application.

Thus the entire orthopaedic experience extant serves to prove that the most reliable of all known and possible variants of regeneration of the functioning of the joint is the recreation by the surgeon of a natural live joint. Unfortunately, this method of restoring joints could so far not be successfully used, as there was no possible way of growing hyaline cartilage of the joints.

It is an object of the present invention to provide an orthopaedic endoapparatus adapted to purposefully connect through a kinematic linkage, the joint ends of a provisional shoulder and hip joint made by milling, thus allowing it to actively perform only those movements, which are essential for the formation of a new joint of the required shape and function, so that whether at rest or engaged in movements, this apparatus should maintain a clearance between the facies articularis indispensable for their converging congruent and complementary natural growth, which ends in covering the facies articularis by hyaline cartilage capable to exercise its supporting function.

It is another object of the invention to provide an orthopaedic apparatus capable of a sparing mechanical setting of pathologically dysplastic and congenitally luxated hip joints in children and of securing thereafter the caput of the joint in a kinematic position, indispensable for the natural reforming of the joint in the process of the child's growth.

These objects are attained in an orthopaedic endoapparatus designed to grow a new live shoulder or hip joint, to reconstruct a deformed joint or to restore a pathologically dysplastic and congenitally luxated joint, wherein provision is made, according to the invention, for a figured hinge, consisting of a spherical knob in sliding engagement with a curved guiding member having a hollow of a circular cross-section corresponding to the spherical knob and ensuring limited turning of the spherical knob, its position on the rotation axis of the caput in one plane, and its gliding along the guiding member along an arc with its radius from the rotation axis of the caput in another plane. The latter is to be placed on the bone close to the provisional joint provided by milling. A curved rod connects the spherical knob with one end of an expandable turnbuckle. Its other end is detachably and controllably connected with an anchor-like pair of detachable crosswise interconnected curved rods. These are to be attached to the hip or shoulder bone by introducing them into the bone tube to form three support areas on the compact layer of opposite sides within the tube wall. The curved guiding member is rigidly fixed by its back side to one end of the rod, while the other end thereof is detachably and controllably fastened to a similar anchor-like member, consisting of detachably crosswise connected rods to be attached to the pelvis, or the scapula and clavicula. As the apparatus is fixed to the bones forming an articulation, the joint ends of the bones are set in a position which makes possible purposeful active movements around a predetermined point or some axes, that are indispendable for the joint in question in accordance with the required shape and function, with the maintenance of a clearance between the facies articularis, indispensable for their congruent and complementary counter-directed natural growth, finally covering the facies articularis by supporting articular hyaline cartilage.

It is expedient that the expandable connecting turnbuckle should contain a sleeve, having outside flats for a spanner, and a longitudinal tubular bore throughout its inside. The middle portion of said bore has a plain cylindrical surface, while the end portions thereof are provided with opposite-hand screw threads for two threaded rods screwed into the sleeve from opposite ends. Both rods have plain end portions located inside the sleeve and having a diameter inferior to that of the bore of said sleeve, these end portions being lengthwise reduced for a thickness less than half their diameter and for a length exceeding that of the entire plain-bore terminal portion by about the diameter of the threading. The reduced terminal portions of the rods are in mutual engagement with their flat surfaces, while the cylindrical surfaces thereof are in contact with the surface of the bore within the sleeve, thus mutually pushing each other off the longitudinal axis of the sleeve and thereby forming a preloaded contact between the rods, as well as between the rods and the sleeve, whereas the basal threaded portions of the longitudinally reduced end parts of the rods are bent aside from the longitudinal axis of the sleeve to form oppositely directed screw-threaded halfcones that wedge the threading on their cylindrical surfaces radially into the threading on both end portions of the sleeve. The end of one of the threaded rods coming out of the sleeve passes directly into the bent rod already mentioned, connected with the spherical knob, while the end of the other threaded rod coming out of the sleeve terminates in a toothed segment that engages the projection of one of the curved rods of the anchor-like couple, said segment having at its base a taper hole adapted to engage the taper projection of the other curved rod of the anchor-like couple, and braced by means of a screw with said toothed segment, so as to form the afore-said detachable cone-shaped toothed interconnection of the anchor-like couple of curved rods with the expandable turnbuckle, which carries also a collar, braced by a screw with its end pointed into a drill-bit, adapted to be screwed into the bone.

The afore-said expandable connecting turnbuckle precludes the rotation of the threaded rods relative to each other, the self-loosening of the appliance under the strain of a variable load and any longitudinal or transversal play in the turnbuckle. The strength of the connection at rest, as well as over the entire working distance of the turnbuckle remains equal to the strength of the round portion of the screw-threaded rods. As a result, the turnbuckle ensures setting of the hip or shoulder bone in the optimum position and their immovable fixation in relation to the turnbuckle.

The collar attached to the turnbuckle gives added strength to the fastening of the turnbuckle to the hip or shoulder bone. The collar also assists in the fixation of the lowered trochanter to the hip bone.

It is quite practicable to provide the anchor-like fixation member with two curved rods, of which the rod connecting the guiding member with the anchor-like fixation member would be screw-threaded to engage the sleeve provided with a closed threaded aperture and having on its outside the flats for a spanner, as well as longitudinal slits on the end portion facing the guiding groove and braced by a collar with a screw which has a drill-bit end for being screwed into the bone, while the other end portion of the sleeve terminates in a spherical knob held in between the branches of a clamp thrust upon by a screw which, when turned in at the same time engages the longitudinal threaded hole in the taper projection of one of the curved rods that form the anchor-like fixation member adapted to engage the taper hole in one of the branches of the tongs while the other branch terminates in a toothed segment adapted to engage the projection of the other curved rod of said anchor-like member, thus forming said detachable and controllable, cone-shaped toothed, interconnection of the rod which is attached to the guiding member, and of the anchor-like member for fixation to the bone.

Such an embodiment of the rod linking the guiding member with the anchor-like fixation member allows one to set the guiding member accurately into a required position with regard to the articular fossa and, thereby, bring about in the provisional joint the most favourable conditions for its natural complementation according to the intended shape and function.

The afore-described embodiment of the anchor-like couple allows one to establish a preloaded system of fixation of elastically coupled rods to a fragile bone. This does not bring about the destruction of the spongy structure and of the system of innervation and circulation within the bone, hence the bone will not be devitalized by operative trauma. The contact stress arising in this system of fixation has an irritating (as opposed to destructive) level for the live bone tissue, hence bone tissue proliferates, by way of compensation, within an area of contact support with metal, which leads in due course to an increasingly strong bone-to-metal joint.

The anchor-like fixation member may also include three detachably crosswise interconnected curved rods, braced by a screw to one another and to the end of the rod connected with the guiding member. Such an embodiment of the anchor-like fixation member is most efficient in fixing the apparatus to the scapula and the clavicula, though it can also be used upon the pelvis.

The orthopaedic endoapparatus designed to grow a new live shoulder or hip joint, to reconstruct a deformed joint or to restore a pathologically dysplastic and congenitally luxated joint provides for conditions necessary for raising new live supporting articular hyaline cartilage, identical to the natural one, upon the facies articularis provisionally prepared by milling the joint ends of the patient's bones forming the new joint, and thus opens up the possibility of growing a new live joint according to predetermined form and function in place of the lost one (ankylosis) or at a certain distance from it, where the bone is being split, joint ends are provisionally milled, and where there exist, or are plastically adjusted, muscles for the performance of active movements by the patient's will in this new shoulder or hip joint of man. The said apparatus is likewise used for the reconstruction of deformed shoulder or hip joints. The apparatus mechanizes the process of sparingly resetting a pathologically dysplastic and congenitally luxated hip joint in children and adjusts the position and movements of the ends of the joint during the child's growth until the period of the natural reforming of the joint is completed.

The afore-said apparatus unites purposefully kinematically the underdeveloped joint ends of the congenitally luxated hip joint of children, previously adjusted with the assistance of the same apparatus, as well as provisionally created by milling new or reconstructed ends of shoulder or hip joints of adult or juvenile patients, in maintaining between the facies articularis, whether they be in rest or are being moved, a clearance indispensable for their counterdirected, congruent and complementary natural growth.

In controlling the position and movements of the joint the apparatus does not allow movements that are chaotic or unnecessary for the respective joint, permitting in the provisional joint only those movements around a predetermined point or some axes that are needed for the growing of the joint according to predetermined form and function.

Under these conditions patients, enjoying a free regimen, develop within six to twelve months a new joint, the ends of which are congruent and shaped so as to correspond to the predetermined function of the joint, while the facies articularis of its caput and fossa have been covered by supporting hyaline cartilage 1.5 to 2 mm thick on each surface of the joint. This cartilage has a white, smooth, moist, shiny surface, and has firmly grown together with the underlying bone tissue of the joint ends.

Histological analysis of some fragments of cartilage, taken at the biopsy from a new joint during the operative removal of the apparatus, prove that the faciae articularis of the new live joint, grown with the assistance of the proposed apparatus, are actually covered by young hyaline cartilage tissue, which is in some places underdeveloped and forms in other places focal points of newly developing cartilage and bone tissue. The results of histological research permit one to speak of newly developed live articular hyaline cartilage.

Articular hyaline cartilage is the fundamental structural element that serves to distinguish the new live joint from the hitherto known artifical and pathological movabilities between the fragments.

In addition, the new live joint is surrounded by the joint capsule containing the synovial fluid.

The new live shoulder or hip joint, formed with the assistance of the herein-proposed apparatus, is set in motion actively by the patient's will.

After the new joint has been finally formed and the apparatus removed, patients are able to do physical work and are even employed as motor-vehicle drivers.

In what follows the invention is illustrated in greater detail in a disclosure of a specific embodiment of the apparatus, given by way of example with reference to the accompanying drawings, wherein:

FIG. 3 is a cross-sectional view along the line III — III of FIG. 2, with the axes of both turnbuckles in the plane of the cross-section;

FIG. 4 is a cross-sectional view along the line IV—IV of FIG. 3;

FIG. 5 is an embodiment of the endoapparatus designed to grow a new live right joint, preferably a shoulder joint according to the invention, as shown in the position of attachment to the bones forming the shoulder joint, front view; and FIG. 6 is the same endoapparatus, side view, partly in cross-section.

Figure 1:
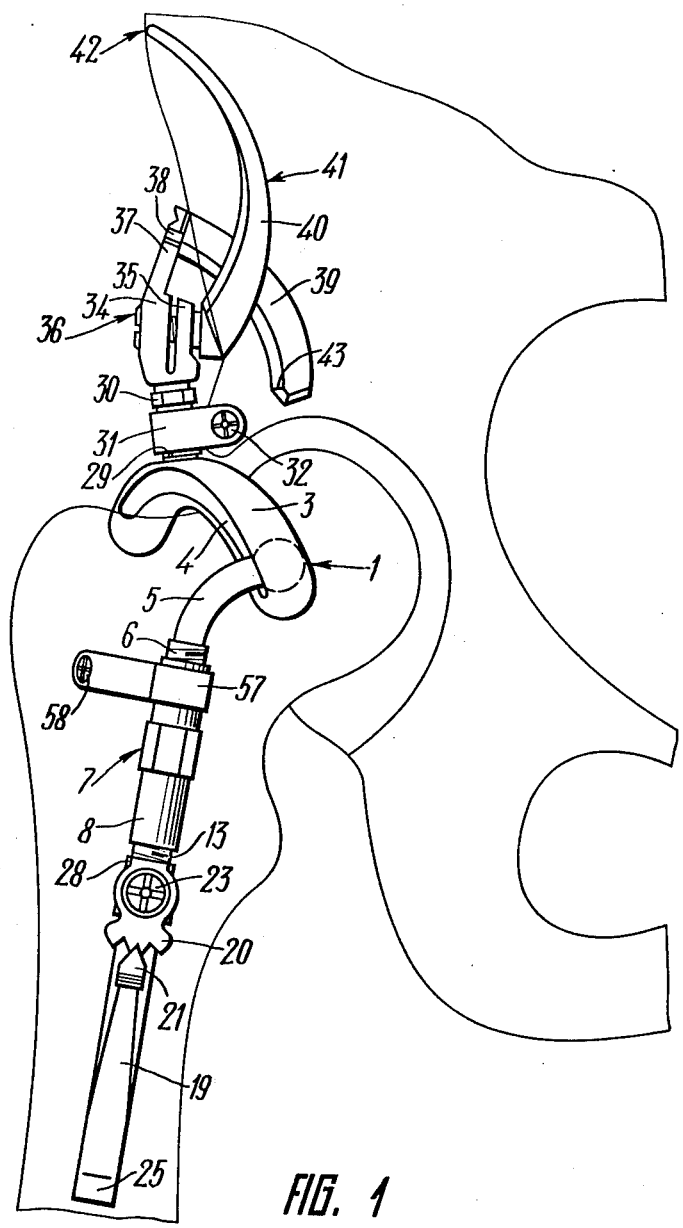
FIG. 1 represents an orthopaedic endoapparatus designed to grow a new live right joint, preferably a hip joint, to reconstruct a deformed joint or to restore a pathologically dysplastic and congenitally luxated joint according the invention, shown in the position of attachment to bones forming the joint, front view.

The proposed endoapparatus designed to grow a new live shoulder or hip joint, to reconstruct a deformed joint or to restore a pathologically dysplastic and congenitally luxated joint has a figured hinge 1 (FIGS. 1,2), consisting of a spherical knob 2 in sliding engagement with the interior surface of a curved guiding member 3. The curved guiding member 3 has a hollow interior 4 of a circular cross-section, corresponding to the spherical knob 2 and ensuring limited turning about the center of the spherical knob 2, its position on the rotation axis of the caput in one plane, and its sliding along the member 3 along an arc with its radius from the rotation axis of the caput in another plane. The spherical knob 2 is attached to one end of a rod 5, the other end of which forms a cylindrical threaded rod 6 of an expandable turnbuckle 7.

The turnbuckle 7 contains a sleeve 8 (FIG. 3) having flats 9 (FIG. 4) for a spanner on the outside thereof.

The sleeve 8 of the turnbuckle 7 (FIG. 3) has a longitudinal bore thereinside. A middle portion 10 of this bore has a plain cylindrical surface with a diameter D (FIG. 4), while end portions 11 and 12 adjoining same have right and left threading, respectively.

The threaded rods 6 and 13 screwed from opposite ends into the sleeve 8 have plain end portions 14 and 15 thereinside (FIGS. 3 and 4), the diameter $d$ of which (FIG. 4) is inferior to the diameter D of the longitudinal bore of the sleeve 8. The end portions 14 and 15 of the rods 6 and 13 (FIG. 3) are longitudinally reduced for a thickness less than their cross-section, over a length that exceeds the entire length of the plain-bore end portions 14 or 15 about the diameter of the threading. The reduced flat end portions 14 and 15 of the rods 6 and 13 are in mutual engagement, while their cylindrical surrfaces are in contact with the walls of the middle portion 10 of the sleeve 8.

As the heights $h$ and $h_1$ (FIG. 4) of the cylindrical longitudinally reduced end portions 14 and 15 exceed half their diameter $d$, they mutually push each other away from the longitudinal axis of the sleeve 8. The longitudinally reduced end portions 14 and 15 therefore form a preloaded contact between the rods 6 and 13 (FIG. 3) on the plane of the contact, as well as between the rods 6 and 13 and the sleeve 8 in its plain middle portion 10. The threaded basal portions 16 and 17 of the longitudinally reduced end portions 14 and 15 of the rods 13 and 6 are bent aside from the longitudinal axis of sleeve 8, form oppositely directed screw-threaded half-cones that wedge their threading into the threading of sleeve 8 along both its end portions 11 and 12.

Such a construction of the connecting turnbuckle 7 precludes, at rest as well as over the entire working distance of the turnbuckle, which is equal to half the length of the sleeve 8, the rotation of the rods 6 and 13 relative to each other, precludes transversal and longitudinal play between the rods 6 and 13 and between the rods 6 and 13 and the sleeve 8 in the threading, and, what is particularly important, precludes any possibility of self-loosening of the connection without any additional stopping appliances being used. At the same time the tensile, compressive, torsional and twisting strengths of the connection remain equal to those of the cylindrical portions of the rods 6 and 13.

The endoapparatus is fastened to the shoulder or hip bone by an anchor-like pair of curved rods 18 and 19 (FIG. 2), which are detachably crosswise connected with each other by the rod 18 being passed through an aperture in the rod 19.

Figure 2:
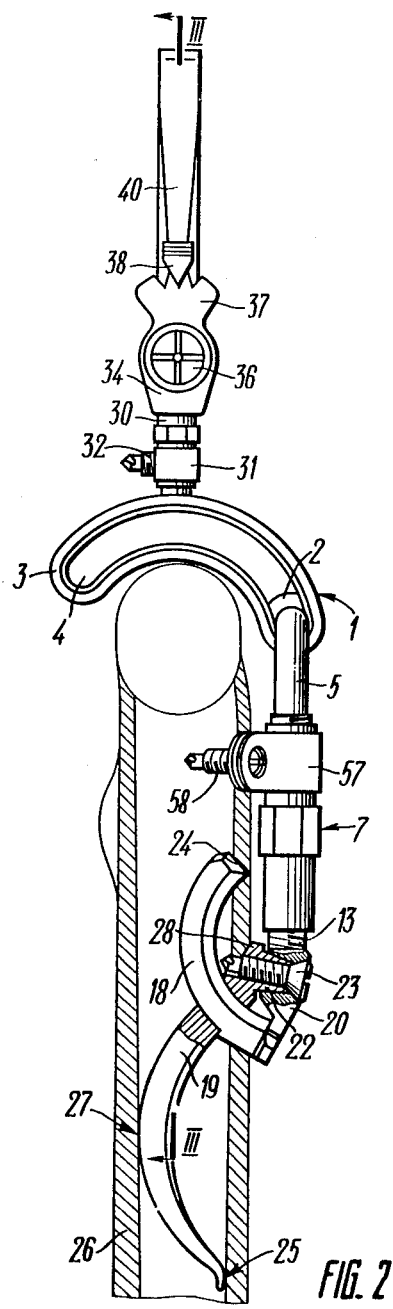
FIG. 2 is the same endoapparatus, side view, partly in cross-section.

The end of the threaded rod 13 on issuing from the sleeve 8 is terminated in a toothed segment 20 (FIGS. 2 and 3) hooked up with a projection 21 (FIG. 3) of the curved rod 18 (FIG. 2), the other curved rod 19 having a taper projection 22, which is engaged with the taper hole at the base of the toothed segment 20, and the curved rod 19 is braced with the toothed segment 20 by a screw 23. As a result there is formed the detachable and controllable cone-shaped toothed interconnection of the anchor-like couple of curved rods 18 and 19 with the expandable connecting turnbuckle 7. Ends 24 and 25 of the crosswise connected curved rods 18 and 19 spread out from the point of intersection in opposite directions, and, on being inserted into a bone tube 26, form on the inside two support areas on one side, while a middle portion 27 of the rod 19 forms a third support area within the bone tube 26 upon the compact layer of its wall on its diametrically opposite side. The rod 19 engages upon the outside surface of the bone tube 26 by its quadrangular area 28 (FIGS. 2 and 3), situated at the base of its taper projection 22 (FIG. 2).

By being inserted into the bone tube 26 the rods 18 and 19 are set into a preloaded condition with each other and between themselves and the bone tube 26.

Such a preloaded system of fixation of the compact layer of the fragile-elastic bone with the elastic interconnected rods 18 and 19 ensures the enduring solidity of bone-to-metal linkage with a three to ninefold margin of safety for the bone against crushing under conditions of variable strain.

The curved guiding member 3, designed to limit the positions and directions of movement of the spherical knob 2 which it contains, is on its outside fixedly connected with one end of a threaded rod 29 (FIG. 3). The other end of the rod 29 is screwed into a sleeve 30. On the outer surface of the sleeve 30 there are flats for a spanner. The end portion of the sleeve 30 facing the guiding member 3 has three longitudinal slits, and this part of the sleeve is braced by a collar 31 with a screw 32 (FIGS. 2 and 3) ending as a drill-bit to be screwed into the pelvis.

Bracing by the screw 32 ensures the tight fixation of the sleeve 30 and the rod 29 (FIG. 3).

The sleeve 30 is terminated in a spherical knob 33. The spherical knob 33 is held in a clamp between the gripping jaws 34 and 35 thereof, braced by a screw 36. When the screw 36 is tightened, the space between the jaws 34 and 35 is narrowed, and the spherical knob 33 is fixed immovably. The branch 34 is terminated in a toothed segment 37 (FIG. 2), hooked up with a projection 38 of a curved rod 39. The curved rod 39 is detachably and crosswise linked with a curved rod 40 by being passed through an aperture in the rod 40. The rods 39 and 40 form an anchor-like fixation member adapted to fix the apparatus mainly to the pelvis. Support areas 41, 42 and 43 (FIG. 1) are intended to lean against the bone.

The curved rod 40 has on its end a taper projection 44 (FIG. 3), which is inserted into the taper aperture in the branch 35. Through the taper projection 44 a threaded hole has been drilled, into which the screw 36 is turned, tightening the branches 34 and 35. Thus is formed a detachable and controllable cone-shaped and toothed interconnection of the rod 29, coupled with the guiding member 3, to the anchor-like member for fixation of the apparatus to the pelvis.

Such a construction connecting the figured hinge 1 of the apparatus and the anchor-like pair of curved rods 39 and 40 in order to fasten the apparatus to the pelvis, allows the surgeon to set the figured hinge 1 at the right place with regard to the articular fossa, and also allows him to use it as a jack for a sparing resetting of congenitally luxated joints in children.

If the proposed apparatus is to be used for the growing of a new live shoulder joint, it is advisable to change somewhat the anchor-like member for fixation of the apparatus to the clavicula and the scapula, as shown in FIGS. 5 and 6.

In this case the back side of the guiding member 3 is connected with an expandable turnbuckle 45 (FIG. 5), thus associating the figured hinge 1 with the anchor-like member for fixation of the apparatus to the scapula and clavicula.

The connecting turnbuckle 45 consists of a sleeve 46 having an end-stopped longitudinal threaded bore thereinside. The closed end of the sleeve is immovably attached to the back side of the guiding member 3, while the other end of the sleeve receives a threaded rod 47. The rod is provided with a nut 48, the other end of the rod terminates in a flat toothed segment 49 (FIG. 6). A transversal aperture is provided in the rod 47 at be base of the segment 49. The body of said sleeve 46 has a longitudinal slit, while to narrow this slit in order to get the turnbuckle fixed in the desired position, the sleeve is provided with a collar 50, braced by a screw 51. The screw ends as a drill-bit to be screwed into the bone.

The anchor-like member for fixation to the scapula and the clavicula consists of three curved rods 52, 53 and 54, which are detachably and controllably crosswise connected with one another and with the free end of the rod 47 of the turnbuckle 45, which runs from the back of the guiding member 3.

The rod 54 of the aforementioned anchor-like fixation member has in its middle portion a transversal threaded aperture. One end of the rod 54 is bent into a claw for insertion into the acromial appendage of the scapula, while the other end of this rod is straight and terminates in a tooth-like projection 55, adapted to hook up with the toothed sector 49 of the turnbuckle 45 (FIGS. 5 and 6). When the anchor-like member is mounted, the rod 54 is placed below (FIG. 5), while the other two rods extend to the left (52) and to the right (53). One end of each of the lateral rods 52 and 53 is cleft into an upper and a lower branch, both traversed by a transversal aperture. When mounting the rods 52 and 53 they are set by their branches upon the flat area of the rod 47 of the turnbuckle 45, so that the transversal aperture in the rod coincides with the apertures in the branches. The branches of the lateral rods are set upon each other, while the interval between the upper and lower pair of branches is occupied by the rod 47 of the turnbuckle 45. A screw 56, upon passing the superposed apertures, is turned into the threaded aperture in the rod 54. Thus, a detachable and controllable connection between the rods of the anchor-like member for fixation to the bones is formed, as well as the linkage of this member to the sleeve 45, setting out from the figured hinge 1. The curved rods 52 and 53 have sharp hook-shaped ends. The rod 53 embraces with this end the acromial part of the clavicula from the front and from below, while the rod 52, upon embracing the upper edge of the scapula, is driven with its pointed end into the scapula from behind (not shown). In this position the rods 52 and 53 are tightened and made fast by the nut 48 (FIGS. 5 and 6).

The expandable turnbuckle 7 has a collar 59, braced by a screw 60 ending as a drill-bit to be screwed into the bone.

For each joint or symmetrical pair of joints, which have their own unique form and function, the apparatus must have a construction suited to the demands of form and function of the respective joint.

For each symmetrical pair of joints a pair of apparatus are prepared as a mirror reflection of each other. For children, adolescents and adults the apparatus must be available respectively in three different sizes. The closest correspondence of the apparatus with the size of the bone is obtained by regulating the movably and controllably connected parts of the apparatus.

The operation of provisional shaping of the ends of the joints by milling them out of the live bone of the patient in the place of cloven anthylosis or of reconstruction of deformed ends of the joints is performed under general narcosis.

After typical resection of soft tissues and the preparation of the place of the lost joint or of the deformed ends of the joint, provisional joint ends are made by milling.

The anchor-like fixation members of the apparatus are inserted respectively into both bones forming the joint. In operations on the hip the curved rods 18 and 19 are inserted into the bone tube 26 of the hip bone, the curved rods 39 and 40 (FIG. 1) into the pelvis. After that the anchor-like fixation members are joined by the rest of the apparatus, i.e., the expandable connecting turnbuckle 7 is linked up with the curved rods 18 and 19 (FIG. 2), and the rod 29 (FIG. 3) of the turnbuckle 30, held in between the branches 34 and 35 of the clamp, with the rods 39 and 40. As a result, the curved rod 5 and the curved guiding member 3, movably interconnected by the spherical knob 2, restrict the position of the femoral neck, as the curved rod 5 is fastened to the neck from before, while the guiding groove 3, having the shape of a part-ring, restricts the neck from before and from behind.

By turning the sleeve 8 of the turnbuckle 7 and the turnbuckle 30, and by finding out the angle needed for engaging the toothed segments 20 and 37, the correct kinematic position between the provisional ends of the joint has to be established, providing for the clearance needed for their conjunctive growth.

Having ascertained that the bone ends of the joint are in the best possible position, the surgeon renders the chosen position rigid by tightening all the screws of the apparatus.

If it is the shoulder joint that is to be operated, the way to proceed is similar to the afore described operation of the hip joint, but in this case it is expedient to use that type of apparatus, where the anchor-like member for fixation to the scapula and the clavicula consists of the three curved rods 52, 53, 54 (FIGS. 5 and 6).

The curved rod 54 is driven into the acromial appendage of the scapula. In the case of a right joint, the rod 53 encircles the acromial end portion of the clavicula, while the curved rod 52, upon embracing the edge of the scapula from the front and from behind, has its sharp point driven into the bone tissue of the scapula. After that the surgeon chooses the suitable angle for hooking up the toothed sector 49 with the curved rod 54 and finally tightens the screw 56.

The position of the curved rods 52 and 53 is fixed by the nut 48.

By regulating the length of the expanding connecting turnbuckles 7 and 45 and choosing the suitable angle of engagement for the toothed segments 20 and 49, (FIGS. 5 and 6) the joint end of the shoulder-bone is set into the best possible kinematic position relative to the provisional joint surface of the scapula. Between the provisional surfaces of the joint there is left a clearance essential for their conjunctive complementary growth.

Thus, the described regulative adjustment of the position of the apparatus allows one to establish the joint ends of the bones in a position needed for kinematics with a sufficient clearance between the provisional facies articularis, essential for their natural congruent and complementary growth, terminated when the facies articularis become covered with supporting hyaline cartilage of the joint. This comes about 6 to 12 months after the operation resulting in the provisional formation of a new joint by milling provisional ends of the joint out of the patient's live bone in place of the lost joint or at a certain distance there from, where there are muscles or where they may be plastically adapted to bring the new joint in motion by the patient's will.

The post-operational regimen of the patient is free, movements begin in the operated joint immediately after the operation and become gradually more sweeping as the aseptical inflammation subsides. After the removal of suture from the skin wound the patient is allowed to go home, where he continues his curative physical exercises.

After the final formation of the joint the apparatus is removed, but patients of more than 60 may retain the apparatus for life, as it does not interfere with their daily existence or their work.

We claim:

1. An orthopaedic endoapparatus designed to grow a new live shoulder or hip joint, to reconstruct a deformed joint or to restore a pathologically dysplastic and congenitally luxated joint, including: a figured hinge designed to be placed upon the bone close to a provisional joint created by milling; said figured hinge having a spherical knob and a curved guiding member having a hollow interior in which said spherical knob is located, said hollow interior being of a circular cross section, corresponding to the shape and size of said spherical knob and ensuring restricted rotation of said spherical knob, its position on the rotation axis of the caput in one plane, and of its sliding along said guiding member along an arc with its radius from the rotation axis of the caput in another plane; a curved rod having one end to which said spherical knob is fastened; an expandable connecting turnbuckle having one end connected with a second end of said curved rod; an anchor-like pair of separably crosswise interconnected members, separably and controllably linked with a second end of said expandable connecting turnbuckle and designed to be fixed to the hip-bone or shoulder-bone so as to form there three support areas upon the compact layer of opposite walls inside the bone tube; a second rod, one end of which is firmly fixed to an outer side of said guiding member; an anchor-like member for fixation to the pelvis or the scapula and clavicula, fixed separably and controllably to a second end of the second rod; said anchor-like fixation member having curved members separably crosswise interconnected, designed for fixation to the pelvis or the scapula and clavicula; as a result of which when fixing the apparatus to the bones forming the joint, the joint ends of the bone are established in a position making possible purposeful active movements within the joint around a definite point or axis, indispensable for the respective joint in accordance with the predeterminate form and function, ensuring the maintenance of a clearance between the faciae articularis as being necessary for their natural congruent and complemental conjunctive growth, coming to term by covering the faciae articularis with support-giving hyaline cartilage.

2. An orthopaedic endoapparatus according to claim 1, including: a sleeve of said expandable connecting turnbuckle; flats for a spanner on the outer surface of said sleeve; a collar mounted on said sleeve; a screw tightening said sleeve and ending in a drill-bit to be screwed into the bone; said sleeve being penetrated throughout by a longitudinal bore having a middle portion provided with a smooth cylindrical surface and end portions provided one with right-hand, the other with left-hand threading; two threaded strainers, screwed into said sleeve from opposite ends and having inside said sleeve plain end portions of a diameter less than the diameter of said longitudinal bore of said sleeve and being longitudinally reduced to a thickness less than half their cross-section, and over a length exceeding the length of the entire plain end portion by about the diameter of the threading on said threaded strainers, said plain end portions respectively having flat reduced surfaces engaging each other and outer cylindrical surfaces engaging the surface defining said longitudinal bore of the sleeve, thus mutually pushing each other away from the longitudinal axis of the sleeve and forming thereby a preloaded contact between said threaded strainers, as well as between the threaded strainers and the sleeve, basal parts of said longitudinally reduced end portions of the strainers forming oppositely directed threaded half-cones, wedging the threading on their cylindrical surfaces into the threading of said end portions of the longitudinal bore of the sleeve; one of the threaded strainers having an end running out of said sleeve and passing directly into said curved rod, connected with said spherical knob; the other of said threaded strainers having an end running out of said sleeve and provided with toothed segments and being formed with a taper aperture at the base of said toothed segments; one of said curved members of said anchor-like fixation member engaging said toothed segments; a second of said curved members of said anchor-like fixation member having a taper protrusion engaging said taper aperture; a screw bracing said second curved member of the anchor-like fixation member with said toothed segments, as a result of which there is formed said separable and controllable connection of said curved members of said anchor-like fixation member with said expandable turnbuckle.

3. An orthopaedic endoapparatus according to claim 1, including: a strainer immovably fixed to the outside of said guiding member and provided with threading; a turnbuckle with a threaded aperture into which said strainer is screwed; flats for a spanner upon the outer surface of said turnbuckle; said turnbuckle having one end portion turned toward said guiding member and formed with longitudinal slits; a spherical knob on the other end of said turnbuckle; a clamp having two branches grasping said spherical knob with one of said branches having toothed segments, one of said curved members of the anchor-like fixation member engaging with said toothed segments; the other of said branches having a taper aperture; a taper protrusion on a second of said curved members of the anchor-like fixation member engaging with said taper aperture and formed with a threaded aperture; a screw tightening said clamp branches and being screwed into said threaded aperture in said taper protrusion, as a result of which there is formed a separable and controllable toothed interconnection of said strainer, connecting said guiding member with said anchor-like fixation member for fixation to the bone.

4. An orthopaedic endoapparatus according to claim 2, including: a threaded stainer immovably attached to the outside of said guiding member; a turnbuckle with a threaded bore into which said latter strainer is screwed; flats for a spanner on the outer surface of the latter turnbuckle; one end portion of said last-mentioned turnbuckle being turned toward said guiding member and having longitudinal slits; a collar mounted on said last-mentioned end portion of said turnbuckle; a screw bracing said collar and having a drill-bit ending for screwing into the bone; a spherical knob at the other end of said last-mentioned turnbuckle; a clamp having two branches grasping the latter spherical knob; one of said curved members of said anchor-like fixation member having a projection; toothed segments upon one of said branches engaged by said projection of said one of said curved members of the anchor-like fixation member; the second of said branches having a taper aperture; a taper protrusion on a second of said curved members of the anchor-like fixation member engaging said taper aperture and having a threaded aperture; a screw tightening said clamp branches by being screwed into said threaded aperture of said taper protrusion, as a result of which there is formed said separable and controllable interconnection of said strainer connecting said guiding member with said anchor-like member for fixation to the bone.

5. An orthopaedic endoapparatus according to claim 1, said anchor-like fixation member having three curved members; a screw bracing together said three curved members and bracing them with an end of a strainer immovably attached to said guiding member.

6. An orthopaedic endoapparatus according to claim 2, including: three curved members of the said anchor-like fixation member; a screw, bracing said three curved members with one another, and with an end of a strainer immovably attached to the guiding member.

* * * * *